US008883460B2

(12) United States Patent
Cho et al.

(10) Patent No.: US 8,883,460 B2
(45) Date of Patent: Nov. 11, 2014

(54) L-ORNITHINE OR L-ARGININE PRODUCING STRAIN AND METHOD FOR PRODUCING L-ORNITHINE OR L-ARGININE

(75) Inventors: Jin-Man Cho, Seongnam-si (KR); Hye-Won Kim, Seongnam-si (KR); Ji-Hye Lee, Anyang-si (KR); Jae-Yong Cho, Wonju-si (KR)

(73) Assignee: CJ Cheiljedang Corp., Seoul (KR)

( * ) Notice: Subject to any disclaimer, the term of this patent is extended or adjusted under 35 U.S.C. 154(b) by 0 days.

(21) Appl. No.: 13/512,956

(22) PCT Filed: Dec. 29, 2010

(86) PCT No.: PCT/KR2010/009521
§ 371 (c)(1),
(2), (4) Date: Oct. 11, 2012

(87) PCT Pub. No.: WO2011/083933
PCT Pub. Date: Jul. 14, 2011

(65) Prior Publication Data
US 2013/0023016 A1    Jan. 24, 2013

(30) Foreign Application Priority Data
Jan. 6, 2010   (KR) .................. 10-2010-0000726

(51) Int. Cl.
| *C12P 13/10* | (2006.01) |
| *C12N 1/21* | (2006.01) |
| *C12N 9/10* | (2006.01) |
| *C12N 9/80* | (2006.01) |

(52) U.S. Cl.
CPC ......... *C12P 13/10* (2013.01); *C12Y 203/01001* (2013.01); *C12N 9/1029* (2013.01); *C12N 9/80* (2013.01); *C12Y 305/01016* (2013.01)
USPC ....... 435/114; 435/252.32; 435/227; 435/193

(58) Field of Classification Search
None
See application file for complete search history.

(56) References Cited

U.S. PATENT DOCUMENTS

| 8,216,820 B2 * | 7/2012 | Yukawa et al. .......... 435/252.32 |
| 2002/0045223 A1 | 4/2002 | Suga et al. |
| 2009/0246838 A1 * | 10/2009 | Zelder et al. .................. 435/128 |

FOREIGN PATENT DOCUMENTS

| EP | 0393708 A2 | 10/1990 |
| JP | 57163487 A | 10/1982 |
| KR | 1020060068505 A | 6/2006 |
| KR | 100830289 B1 | 5/2008 |
| KR | 1020100000726 | 1/2010 |
| WO | WO 2009131040 A1 * | 10/2009 |

OTHER PUBLICATIONS

RCSB Potein Data Bank (PDB), Accession No. 2QEC, Jul. 2007, www.rcsb.org/pdb.*
EBI Uniprot, Accession No. Q8NQB1, Oct. 2002, www.uniprot.org.*
Hwang et al., Identification of a suppressor gene for the arginine-auxotrophic argJ mutation in *Corynebacterium glutamicum*, J. Ind. Microbiol. Biotechnol., 2010, 37, 1131-36.*
NCBI GeneBank, Reference Sequence NC_003450.3, for Gene ID 1019499, Locus Tag NCgl1469, Aug. 2003, www.ncbi.nlm.nih.gov/gene.*
Eikmanns et al., A family of *Corynebacterium glutamicum/Escherichia coli* shuttle vectors for cloning, controlled gene expression, and promoter probing, Gene, 1991, 102, 93-98.*
Kind et al., Identification and elimination of the competing N-acetyldiaminopentane pathway for improved production of diaminopentane by *Corynebacterium glutamicum*, Appl. Environ. Microbiol., 2010, 76, 5175-80.*
Amann et al., Tightly regulated tac promoter vectors useful for the expression of unfused and fused proteins in *Escherichia coli*, Gene, 1988, 69, 301-15.*
Ikeda et al., "Reengineering of a *Corynebacterium glutamicum* l-Arginine and l-Citrulline Producer." Appl. Environ. Microbiol. 2009, 75(6): 1635.
Kalinowski et al., "The complete *Corynebacterium glutamicum* ATCC 13032 genome sequence and its impact on the production of L-aspartate-derived amino acids and vitamins." Journal of Biotechnology 2003, 104: 5-25.
Sakanyan et al., "Genes and enzymes of the acetyl cycle of arginine biosynthesis in *Corynebacterium glutamicum*: enzyme evolution in the early steps of the arginine pathway." Microbiology 1996, 142: 99-108.
GCN5-related N-acetyltransferase [*Corynebacterium glutamicum* ATCC 13032]. NCBI Reference Sequence: YP_225811.1, 2013.

* cited by examiner

*Primary Examiner* — Rebecca Prouty
*Assistant Examiner* — Todd M Epstein
(74) *Attorney, Agent, or Firm* — Porzio, Bromberg & Newman, P.C.

(57) ABSTRACT

The present invention relates to a polynucleotide that is active to an acetyl glutamate synthase and acetyl ornithinase which are associated with ornithine or arginine biosynthesis from *Corynebacterium glutamicum*. The present invention also relates to a polypeptide encoded by said polynucleotide, a recombinant vector comprising said polynucleotide, to a transformant obtained by introducing said recombinant vector to a host microorganism for producing L-ornithine or L-arginine, and transforming the recombinant vector, and to a method for producing L-ornithine or L-arginine by culturing said transformant. The activity of the transformant of the present invention to an acetyl glutamate synthase and acetyl ornithinase is increased as compared to an intrinsic activity, and thus L-ornithine or L-arginine can be produced, at a high yield rate, from the transformant of the present invention.

2 Claims, 1 Drawing Sheet

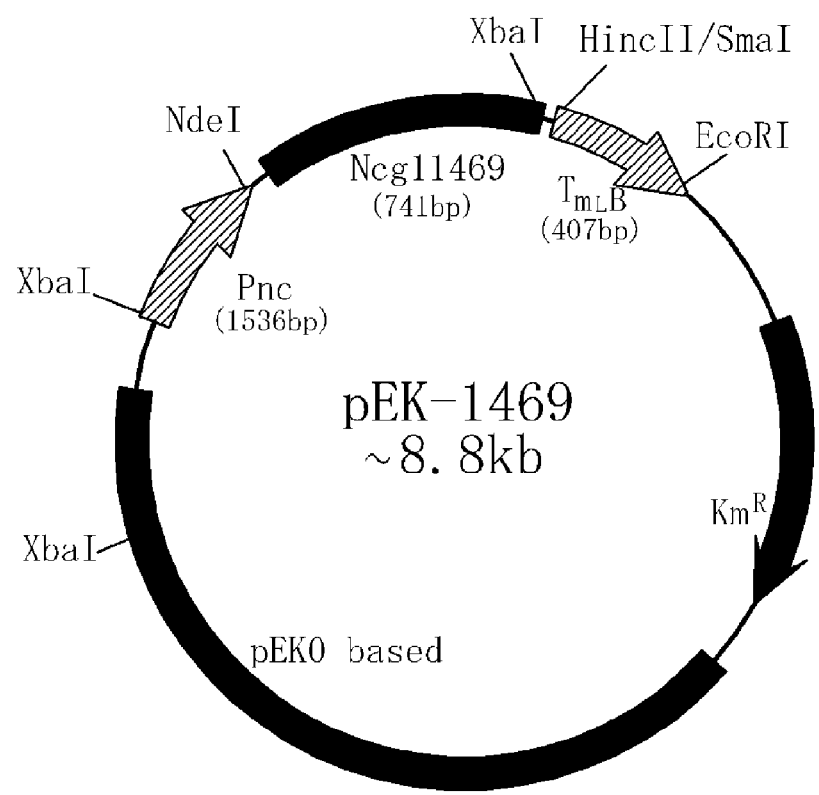

US 8,883,460 B2

L-ORNITHINE OR L-ARGININE PRODUCING STRAIN AND METHOD FOR PRODUCING L-ORNITHINE OR L-ARGININE

TECHNICAL FIELD

The present invention relates to a *Corynebacterium* variant producing L-ornithine or L-arginine and a method for the production of L-ornithine or L-arginine. More particularly, the present invention relates to a *Corynebacterium glutamicum*-derived polynucleotide encoding both acetylglutamate synthase and acetylornithinase which are involved in ornithine or arginine biosynthesis, a polypeptide encoded by the polynucleotide, a recombinant vector carrying the polynucleotide, a transformant prepared by introducing the recombinant vector into a host organism that produces L-arginine, and a method for producing L-ornithine or L-arginine by culturing the transformant.

BACKGROUND ART

L-Amino acids are used as ingredients in medicines for humans and are applied particularly to the pharmaceutical industry and the food industry and are also used as nutrients for animals. Among L-amino acids, L-ornithine, one of the products on the arginine cycle, is known as a medicinal component that enhances liver function (Salvatore et al., 1964). L-Arginine is abundantly found as a free form in plant seeds and garlic and is used as a nutritional supplement in medicinal or food products. Examples of the medicinal applications of L-arginine include anti-hepatotoxic substances, cerebral metabolic enhancers, therapeutics for male infertility, and general amino acid formulations. Representative among the foods to which L-arginine is applied are fish paste additives, health beverage additives and salt alternatives for patients with hypertension.

Fermentation is applied when coryneform bacteria (especially *Corynebacterium glutamicum*) is used in the mass production of amino acids. Due to the high significance thereof in industrial terms, the method of bacterial production of amino acids is continuously being improved upon. Methodological improvements have been achieved with respect to, for example, agitation, oxygen introduction, and the maintenance of sugar concentration during fermentation.

To increase the microbial productivity of amino acids, the selection of suitable microbes is very important L-amino acid-producing strains which are resistant to anti-metabolite substances or auxotrophic for metabolites responsible for the regulation of amino acids may be selected. For example, variants of *Brevibacterium* or *Corynebacterium* spp. which produce glutamate are used to produce ornithine (EP 0 393 708 A3). Also, variants of glutamate-producing *Brevibacterium* or *Corynebacterium* spp. are used to directly produce L-arginine from carbon and nitrogen sources (Japanese Patent Publication NOs. Sho. 57-163487, 60-83593 and 62-265988).

Recombinant DNA technology is also a useful tool by which L-amino acid-producing coryneform strains can be genetically altered to enhance functions associated with the production of L-amino acids. For example, argCJBD, an ornithine biosynthesis gene, may be introduced into and overexpressed in a strain which is incapable of synthesizing arginine and proline (Hwang et al., 2008). Also, a strain may be genetically recombined to inactivate argR, a gene repressing the expression of the arginine biosynthesis operon (U.S. Patent Application Publication No. 2002/0045223A1).

An increase in amino acid productivity can be achieved by reinforcing the biosynthesis of genes of interest. A report has it that the yield of amino acid production can be improved upon by increasing the expression of biosynthesis genes. For example, the overexpression of the arginine biosynthesis gene argF leads to an increased production of arginine (Korean Patent Application No. 10-2004-107215).

In addition, a method for producing L-arginine in which the argD2 gene (Ncgl2355) or (Ncgl0990), a putative gene of acetylornithine aminotrasferase involved in the arginine biosynthesis of *Corynebacterium glutamicum*, is overexpressed to produce L-arginine in high yield is disclosed (Korean Patent Nos. 0830289 and 0830290).

Like this, microbial strains capable of producing ornithine or arginine in high yield may result from the reinforcement of biosynthesis genes, especially genes of the biosynthesis enzymes acetylglutamate synthase and acetylornithinase.

However, acetylglutamate synthase has been found in none of the *Corynebacterium* spp. known thus far. In this invention, the present invention examined a gene which codes for an enzyme responsible for the function of acetylglutamate synthase. It is reported that the polypeptide of the gene has an activity similar to that of acetylornithinase, encoded by argJ. Further, an enhancement in the activity of the gene was found to increase the concentration of ornithine or arginine. Based on these research results, the present invention was accomplished.

DISCLOSURE

Technical Problem

It is therefore an object of the present invention to provide a novel *Corynebacterium*-derived polynucleotide coding for a polypeptide having acetylglutamate synthase or acetylornithinase activity, or the polypeptide encoded thereby.

It is another object of the present invention to provide a strain in which the gene is overexpressed and that has improved productivity for ornithine or arginine.

It is a further object of the present invention to provide a method for producing ornithine or arginine in high concentrations using the strain.

Technical Solution

In accordance with an aspect thereof, the present invention provides a *Corynebacterium glutamicum*-derived polypeptide showing acetylglutamate synthase and acetylornithinase activity.

In the present invention, the gene Ncgl1469 the sequence of which is publicly available via the database of the National Institute of Health was found to encode both acetylglutamate synthase and acetylornithinase. In *Corynebacterium* spp., the gene coding for acetylglutamate has not yet been determined while acetylornithinase is reported to be encoded by argJ (Sakayan et al., 1996). No documents previous to the present invention disclosed that the gene Ncgl1469 encodes both of the two enzymes. Its amino acid and nucleotide sequences are given as SEQ ID NOS. 1 and 2, respectively.

In accordance with another aspect thereof, the present invention provides a vector carrying a gene coding for both acetylglutamate synthase and acetylornithinase. The vector contains an acetylglutamate synthase and acetylornithinase gene. Examples of the plasmids useful as the vector of the present invention include pZ1 (menkel et al), pEkEx1 (Eikmarms et al), pHS2-1 (Sonnen et al), pCG4 (U.S. Pat. No. 4,489,190), pNG2 (Serwold-Davis et al) and pEKO (Eikmanns et al), with preference for pEKO. More preferably, the vector contains the amino acid sequence of SEQ ID NO. 1 or the nucleotide sequence of SEQ ID NO. 2 and is shown in FIG. 1.

In accordance with a further aspect thereof, the present invention provides a microorganism, or a transformant or recombinant cell which is enriched in acetylglutamate synthase and acetylornithinase. In this context, the strain may be one which is already capable of producing L-ornithine or L-arginine before the enhancement of acetylglutamate synthase and acetylornithinase. The transformant may be readily prepared by those skilled in the art according to any known transformation method. As used herein the term "transformation" is intended to refer to the genetic alteration of a cell resulting from the uptake, incorporation, replication and expression of exogenous DNA.

Typical among typical transformation methods are $CaCl_2$ precipitation, the Hanahan method using DMSO (dimethyl sulfoxide) as a reducing agent on the basis of the $CaCl_2$ precipitation, electroporation, calcium phosphate precipitation, plasma fusion, silicon carbide fiber-mediated transformation, agrobacteria-mediated transformation, PEG-mediated transformation, the dextran sulfate method, a Lipofectamine method, and drying/suppression-mediated transformation.

In the present invention, for example, the recombinant vector pEK-Ptrc::1469 was introduced into a host microorganism by electroporation to yield a transformant which was then isolated using antibiotic resistance.

The expression "enhanced over the inherent activity" is intended to mean the superiority of the intracellular activity of the introduced enzymes acetylglutamate synthase and acetylornithinase to the inherent activity. The enhancement of enzyme activity may be achieved by increasing copies of the gene of interest. The number of gene copies may be increased by using a vector such as a plasmid, or by integrating an additional gene into the chromosome. The enhancement of a regulation element that has a positive effect on the expression of the gene may be a way to increase the number of gene copies. The regulation element may enhance the activity of the gene at the transcription level, and may be used particularly for the enhancement of a transcription signal. Alternatively, the enhancement may be achieved at the translation level by, for example, increasing the stability of mRNA. A gene of interest having high activity may be used. The over-expression of a gene of interest may result from an alteration in the composition of the medium. The activity of the gene may be increased by potentiating the promoter therefor or using a stronger promoter. An example of a strong promoter useful in the present invention is a Tac-promoter (Amann et al). The inherent activity of a gene may be enhanced by mutation. Mutation may be induced by a conventional method using UV light or mutagenic chemicals or by a genetic manipulation method based on the deletion, insertion and/or substitution of nucleotide residues. The above-mentioned measures may be combined to enhance the activity of the enzymes.

Of the coryneform bacteria, *Corynebacterium* or *Brevibacterium* spp., may be used in the present invention. Examples of the starting strains suitable for the preparation of the transformed *Corynebacterium glutamicum* variants include the following wild-type strains: *Corynebacterium glutamicum* ATCC13032, *Corynebacterium acetoglutamicum* ATCC15806, *Corynebacterium acetoacidophilum* ATCC13870, *Corynebacterium thermoaminogenaes* FERM BP-1539, *Brevibacterium flavum* ATCC14067, *Brevibacterium lactofermentum* ATCC13869, *Brevibacterium divaricatum* ATCC14020, and L-ornithine-overexpressing variants thereof which lack enzymes involved in the ornithine biosynthesis pathway, such as ornithine carbamoyltransferase, arginine repressor, and/or glutamate kinase, and L-arginase-overexpressing variants thereof which lack an arginine repressor involved in arginine biosynthesis.

In accordance with a further aspect thereof, the present invention provides a method for producing L-ornithine or L-arginine by culturing the transformed microorganism of the present invention. For culturing the microorganism, appropriate media and other culture conditions well known in the art may be employed. Those skilled in the art may readily select or modify suitable culture conditions depending on the microorganisms. They may be cultured, for example, in a suitable manner the examples of which include, but are not limited to, batch culture, continuous culture and fed-batch culture. These various culturing methods may be found in, for example, "Biochemical Engineering" (James M. Lee, Prentice-Hall International Editions, pp 138-176, 1991). The culture may be adjusted in pH by adding a pH adjuster, such as ammonium hydroxide, potassium hydroxide, ammonia, phosphoric acid and sulfuric acid. During the growth of the microorganisms, an antifoaming agent such as a fatty acid polyglycol ester may be used to prevent the formation of foam. To keep the culture in an aerobic condition, the medium may be aerated by introducing oxygen or oxygen-containing gas (e.g., air). The culture medium may be kept at a temperature of from 20° C. to 45° C. and preferably at a temperature of from 25° C. to 40° C. As for the culturing period, it may be extended to the extent that a desired level of L-arginine methionine is obtained and may be on the order of 10 to 160 hrs. So long as it is known in the art, any typical method may be used to isolate L-ornithine or L-arginine from the culture. Examples of the isolation method include centrifugation, filtration, ion exchange chromatography and crystallization. For example, after centrifugation at low speed to remove biomass, the resultant supernatant is subjected to ion exchange chromatography to purify the amino acids of interest.

Advantageous Effects

The present invention, as described above, provides a *Corynebacterium glutamicum*-derived polynucleotide encoding both acetylglutamate synthase and acetylornithinase which are involved in ornithine or arginine biosynthesis, a polypeptide encoded by the polynucleotide, a recombinant vector carrying the polynucleotide, a transformant prepared by introducing the recombinant vector into an L-arginine-producing host microorganism, and a method for producing L-ornithine or L-arginine by culturing the transformant. Showing higher acetylglutamate synthase and acetylornithinase activity than the inherent activity, the transformant is capable of producing L-ornithine or L-arginine and thus finds useful application in the bio-medical industry.

DESCRIPTION OF DRAWINGS

FIG. 1 is a genetic map showing the structure of the vector pEK-Ptrc::Ncgl1469 according to the present invention.

MODE FOR INVENTION

A better understanding of the present invention may be obtained by the following examples which are set forth to illustrate, but are not to be construed as limiting the present invention.

EXAMPLES

Example 1

Ncgl1469 Cloning

PCR was performed using the oligonucleotides of SEQ ID NOS. 3 and 4 as primers, with pTrc99A (Amann et al. 1988) serving as a template, to amplify a trc promoter useful for the preparation of an overexpression vector. Separately, an rmB terminator was amplified by PCR using the oligonucleotides of SEQ ID NOS. 5 and 6, with pTrc99A serving as a template. The PCR was performed in the presence of PfuUltra™ high-fidelity DNA polymerase (stratagene), with 25 cycles of denaturing at 95° C. for 30 sec, annealing at 55° C. for 30 sec, and extension at 68° C. for 1 min. The nucleotide sequence of NCgl1469 was obtained from the database of the NIH GenBank. On the basis of the sequence, a pair of primers (SEQ ID NOS. 7 and 8) were designed. Using the synthetic primers, PCR was performed on the genomic DNA of *Corynebacterium glutamicum* ATCC13032, with 25 cycles of denaturing at 95° C. for 30 sec, annealing at 55° C. for 30 sec, and extension at 68° C. for 15 min.

The pEKO vector (*E. coli-C. glutamicum* shuttle vector, Eikmanns et al. 1991) was treated with XbaI. Separately, the ptrc promoter and the 1469 ORF, both amplified above, were digested with XbaI, NdeI/NedI, Xba1, respectively, and then ligated to the digested vector to yield a recombinant vector. This was double digested with HincII and EcoRI while the amplified rrnB terminator fraction was treated with SmaI/EcoRI, followed by ligation to afford a recombinant vector in which a promoter—1469 ORF—terminator fraction was inserted.

Example 2

Ncgl1469 Overexpression

To examine the activity of the gene Ncgl1469 cloned in Example 1, first, there was a need for a mutant of *Corynebacterium glutamicum* ATCC13032 in which argJ was disrupted. In this context, the pK18mobsacB integration vector (Schafer et al. 1994) was employed to yield an argJ-disrupted strain. Using two pairs of primers (SEQ ID NOS. 7 and 8; 9 and 10), PCR was performed on the genomic DNA of ATCC13032, with 25 cycles of denaturing at 95° C. for 30 sec, annealing at 55° C. for 30 sec, and extending at 68° C. for 1.5 min. The two PCR products thus obtained were treated with XbaI/ApaI, and ApaI/XbaI, respectively, while the pK18mobsacB vector was digested with XbaI. These resulting three digests were ligated to one another to yield a recombinant vector.

By electroporation, the recombinant vector was transformed into the ATCC13032 strain which was then grown on an agar containing kanamicin at a concentration of 25 mg/L to discriminate strains in which the gene was inserted into the chromosome through homologous recombination. The primary chromosome inserted strain was cultured in a nutrient medium with agitation (30° C., 4 hrs), followed by spreading the strain over agar plates containing sucrose at a 10-fold diluted concentration of from $10^{-4}$ to $10^{-10}$. Most the bacteria died while only a small portion appeared as colonies. The strain which formed colonies was selected as a desired one in which the vector sequence inserted into the chromosome was removed by secondary crossover. The strain was finally selected after it was examined for sensitivity to kanamicin and its gene structure was identified by PCR using the primers of SEQ ID NOS. 7 and 8.

Example 3

Measurement of Ncgl1469 for Acetylglutamate Synthase and Acetylornithinase Activity The strain finally selected in Example 2 was cultured in a broth. After being harvested by centrifugation, the cell mass was washed twice with 100 mM Tris/Hcl buffer (pH 7.5) and lyzed with glass beads to remove membranes.

According to a known method (Envy and Blanchard, 2005), the activity of acetylglutamate was determined by measuring the level of absorbance of 5-thio-2-nitrobanzonate at 421 nm. Also, the activity of acetylornithinase was determined according to a known method (Vogel and Mcleelan, 1970).

The strains obtained by introducing the pEKO vector and the pEK-Ptrc::1469 vector into the strain ATCC13032, argJΔ were induced to overexpress the gene of interest, and the results are summarized in Table 1, below.

TABLE 1

| | | Specific activity (units/mg protein)* | |
|---|---|---|---|
| Strain | Plasmid | Acetylglutamate synthase[a] | Acetylornithinase[b] |
| *C. glutamicum* argJ | pEKO | 0.03 | ND |
| | pEK-Ptrc::1469 | 0.17 | 0.07 |

When the strain which was constructed to lack argJ, a gene known to encode acetylornithinase, was induced to overexpress Ncgl1469, the activities of both acetylglutamate and acetylornithinase were increased, leading to the conclusion that Ncgl1469 encodes both of the enzymes.

Example 4

Ornithine Production of SJ8073-pEK-Ptrc::1469 Strain

To examine the ornithine productivity of the strain in which the gene Ncgl1469 was overexpressed, the ornithin-producing strain SJ8074 (argF-argR-proBΔ, Hwang et al. 2008) was employed as a mother strain.

The strains were cultured in a medium containing 0.8 g/L $KH_2PO_4$, 10 g/L $(NH_4)_2SO_4$, 1 g/L $MgSO_4.7H_2O$, 1.2 g/L $Na_2HPO_4$, 2 mg/L $MnSO_4.H_2O$, 10 mg/L $ZnSO_4.7H_2O$, 10 g yeast extract, 20 g/L $CaCO_3$, 60 g/L glucose and 10 mM IPTG in 250 mL baffle flasks, with agitation. The levels of ornithine in the medium are summarized in Table 2, below.

TABLE 2

| | | L-ornithine concentration (mg/L)[a] | |
|---|---|---|---|
| Strain | Plasmid | Glutamate (0 mM) | Glutamate (50 mM) |
| *C. glutamicum* SJ8074 | pEKO | 137.57 | 145.27 |
| | pEK-Ptrc::1469 | 178.81 | 207.84 |

When Ncgl1469 was overexpressed in the ornithine-producing strain SJ8074, the production level of ornithine was increased by about 20% or more.

The transformant prepared by introducing the recombinant vector pEK-Ptrc::Ncgl1469 into *C. glutamicum* SJ8074 was named *Corynebacterium glutamicum* CA06-0020 and deposited on Dec. 23, 2009 with the Korean Culture center of Microorganisms (hereinafter referral to as "KCCM") under accession number KCCM 11057P.

Example 5

Arginine Production of ATCC21831, argRΔ-pEK-Ptrc::1469 Strain

To examine the organine productivity of the TL2-overexpressing strain, the arginine-producing strain ATCC21831 was modified to lack the arginine repressor argR, and the modified strain was used as a mother strain.

The strains were cultured in media containing 0.8 g/L KH$_2$PO$_4$, 10 g/L (NH$_4$)$_2$SO$_4$, 1 g/L MgSO$_4$.7H$_2$O, 1.2 g/L Na$_2$HPO$_4$, 2 mg/L MnSO$_4$.H$_2$O, 10 mg/L ZnSO$_4$.7H$_2$O, 10 g yeast extract, 20 g/L CaCO$_3$ and 60 g/L glucose in 250 mL baffled flasks, with agitation. The levels of arginine in the media are summarized in Table 3, below.

TABLE 3

| Strain | Plasmid | L-arginine concentration (mg/L)$^a$ | |
|---|---|---|---|
| | | IPTG (0 mM) | IPTG (10 mM) |
| ATCC21831 | pEKO | 1.42 | 1.39 |
| argRΔ | pEK-Ptrc::1469 | 1.39 | 1.56 |

When Ncgl1469 was overexpressed in the arginine-producing strain ATCC21831-argRΔ, the production level of arginine was increased by about 10% or more.

The transformant prepared by introducing the recombinant vector pEK-Ptrc::Ncgl1469 into ATCC21831 argRΔ was named *Corynebacterium glutamicum* CA06-0021 and deposited on Dec. 23, 2009 with the Korean Culture center of Microorganisms (hereinafter referred to as "KCCM") under accession number KCCM 11058P.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

INDUSTRIAL APPLICABILITY

As described hitherto, the present invention provides a *Corynebacterium glutamicum*-derived polynucleotide encoding both acetylglutamate synthase and acetylornithinase which are involved in the ornithine or arginine biosynthesis, a polypeptide encoded by the polynucleotide, a recombinant vector carrying the polynucleotide, a transformant prepared by introducing the recombinant vector into an L-arginine-producing host microorganism, and a method for producing L-ornithine or L-arginine by culturing the transformant. Showing higher acetylglutamate synthase and acetylornithinase activity than the inherent activity, the transformant is capable of producing L-ornithine or L-arginine and thus finds useful application in the bio-medical industry.

The invention claimed is:

1. An isolated *Corynebacterium* sp. strain capable of improved productivity of L-ornithine or L-arginine, which is transformed with a recombinant vector comprising a polynucleotide encoding a polypeptide having an amino acid sequence of SEQ ID NO: 1 to enhance activities of acetylglutamate synthase and acetylornithinase over inherent activity and to increase production of L-ornithine or L-arginine compared to a *Corynebacterium* sp. strain not transformed with a polynucleotide encoding a polypeptide having an amino acid sequence of SEQ ID NO: 1.

2. A method for producing L-ornithine or L-arginine, comprising:
    culturing the *Corynebacterium glutamicum* sp. strain of claim 1; and
    recovering ornithine or arginine from the strain.

* * * * *

SEQUENCE LISTING

```
<160> NUMBER OF SEQ ID NOS: 10

<210> SEQ ID NO 1
<211> LENGTH: 203
<212> TYPE: PRT
<213> ORGANISM: Corynebacterium glutamicum

<400> SEQUENCE: 1

Met Ser Pro Thr Val Leu Pro Ala Thr Gln Ala Asp Phe Pro Lys Ile
1               5                   10                  15

Val Asp Val Leu Val Glu Ala Phe Ala Asn Asp Pro Ala Phe Leu Arg
            20                  25                  30

Trp Ile Pro Gln Pro Asp Pro Gly Ser Ala Lys Leu Arg Ala Leu Phe
        35                  40                  45

Glu Leu Gln Ile Glu Lys Gln Tyr Ala Val Ala Gly Asn Ile Asp Val
    50                  55                  60

Ala Arg Asp Ser Glu Gly Glu Ile Val Gly Val Ala Leu Trp Asp Arg
65                  70                  75                  80

Pro Asp Gly Asn His Ser Ala Lys Asp Gln Ala Ala Met Leu Pro Arg
                85                  90                  95

Leu Val Ser Ile Phe Gly Ile Lys Ala Ala Gln Val Ala Trp Thr Asp
            100                 105                 110

Leu Ser Ser Ala Arg Phe His Pro Lys Phe Pro His Trp Tyr Leu Tyr
        115                 120                 125

Thr Val Ala Thr Ser Ser Ser Ala Arg Gly Thr Gly Val Gly Ser Ala
    130                 135                 140

Leu Leu Asn His Gly Ile Ala Arg Ala Gly Asp Glu Ala Ile Tyr Leu
145                 150                 155                 160
```

```
Glu Ala Thr Ser Thr Arg Ala Ala Gln Leu Tyr Asn Arg Leu Gly Phe
            165                 170                 175

Val Pro Leu Gly Tyr Ile Pro Ser Asp Asp Asp Gly Thr Pro Glu Leu
        180                 185                 190

Ala Met Trp Lys Pro Pro Ala Met Pro Thr Val
        195                 200

<210> SEQ ID NO 2
<211> LENGTH: 612
<212> TYPE: DNA
<213> ORGANISM: Corynebacterium glutamicum

<400> SEQUENCE: 2
atgagtccca ccgttttgcc tgctacacaa gctgacttcc ctaagatcgt cgatgttctg      60
gttgaagcat cgccaacga tccagcattt tacgatgga tcccgcagcc ggaccccggt     120
tcagcaaagc ttcgagcact tttcgaactg cagattgaga agcagtatgc agtggcggga     180
aatattgatg tcgcgcgtga ttctgaggga gaaatcgtcg cgtcgcgtt atgggatcgg     240 ccagatggta atcacagtgc caaagatcaa gcagcgatgc tcccccggct cgtctccatt     300
ttcgggatca aggctgcgca ggtggcgtgg acggatttga gttcggctcg tttccacccc     360
aaattccccc attggtacct ctacaccgtg gcaacatcta gttctgcccg tggaacgggt     420
gttggcagtg cgcttcttaa tcacggaatc gctcgcgcgg gtgatgaagc tatctatttg     480
gaggcgacgt cgactcgtgc ggctcaacta tataaccgtc tgggatttgt gcccttgggt     540
tatatcccct cagatgatga tggcactcct gaactggcga tgtggaaacc gccagcgatg     600
ccaactgttt aa                                                          612

<210> SEQ ID NO 3
<211> LENGTH: 29
<212> TYPE: DNA
<213> ORGANISM: Corynebacterium glutamicum

<400> SEQUENCE: 3
ctagtctaga tcatcaccga aacgcgcga                                         29

<210> SEQ ID NO 4
<211> LENGTH: 34
<212> TYPE: DNA
<213> ORGANISM: Corynebacterium glutamicum

<400> SEQUENCE: 4
ggaattccat atgtctgttt cctgtgtgaa attg                                   34

<210> SEQ ID NO 5
<211> LENGTH: 31
<212> TYPE: DNA
<213> ORGANISM: Corynebacterium glutamicum

<400> SEQUENCE: 5
cccccggggc tgttttggcg gatgagagaa g                                      31

<210> SEQ ID NO 6
<211> LENGTH: 32
<212> TYPE: DNA
<213> ORGANISM: Corynebacterium glutamicum

<400> SEQUENCE: 6
cggaattcaa aaggccatcc gtcaggatgg cc                                     32
```

```
<210> SEQ ID NO 7
<211> LENGTH: 28
<212> TYPE: DNA
<213> ORGANISM: Corynebacterium glutamicum

<400> SEQUENCE: 7
ctagtctaga tccagttcag gaagcacc                                              28

<210> SEQ ID NO 8
<211> LENGTH: 27
<212> TYPE: DNA
<213> ORGANISM: Corynebacterium glutamicum
<220> FEATURE:
<221> NAME/KEY: misc_feature
<222> LOCATION: (1)..(3)
<223> OTHER INFORMATION: n is a, c, g, or t

<400> SEQUENCE: 8
nnngggcccg tgtttgctgg ttagggc                                               27

<210> SEQ ID NO 9
<211> LENGTH: 27
<212> TYPE: DNA
<213> ORGANISM: Corynebacterium glutamicum
<220> FEATURE:
<221> NAME/KEY: misc_feature
<222> LOCATION: (1)..(3)
<223> OTHER INFORMATION: n is a, c, g, or t

<400> SEQUENCE: 9
nnngggccca tgaactcaac gatgcgg                                               27

<210> SEQ ID NO 10
<211> LENGTH: 29
<212> TYPE: DNA
<213> ORGANISM: Corynebacterium glutamicum

<400> SEQUENCE: 10
ctagtctaga cgagcaagtc gatgtagac                                             29
```